United States Patent [19]
Waggener et al.

[11] Patent Number: 5,307,264
[45] Date of Patent: Apr. 26, 1994

[54] METHOD AND APPARATUS FOR COMPUTING TOMOGRAPHIC SCANS

[75] Inventors: Robert G. Waggener, Lytle; Jory D. Lange, San Antonio, both of Tex.

[73] Assignee: W. L. Systems, Inc., San Antonio, Tex.

[21] Appl. No.: 850,346

[22] Filed: Mar. 11, 1992

Related U.S. Application Data

[62] Division of Ser. No. 391,252, Aug. 9, 1989, Pat. No. 5,128,864.

[51] Int. Cl.$^5$ .............................................. G06F 15/00
[52] U.S. Cl. .................................. 364/413.21; 378/14
[58] Field of Search ...................... 364/413.21, 413.13, 364/413.14, 413.15; 378/901, 14, 15

[56] References Cited

U.S. PATENT DOCUMENTS

| | | | |
|---|---|---|---|
| 3,867,634 | 2/1975 | Hounsfield | 378/18 |
| 4,149,247 | 4/1979 | Pavkovich et al. | 364/413.21 |
| 4,212,062 | 7/1980 | Kohno et al. | 364/413.21 |
| 4,365,339 | 12/1982 | Pavkovich et al. | 378/15 |
| 4,570,224 | 2/1986 | Shimoni et al. | 364/413.16 |
| 4,580,219 | 4/1986 | Pelc et al. | 364/413.19 |
| 4,703,424 | 10/1987 | Gullberg et al. | 364/413.21 |
| 4,707,822 | 11/1987 | Hopkinson et al. | 364/413.21 |
| 4,740,896 | 4/1988 | Horiba et al. | 364/413.18 |
| 4,769,757 | 9/1988 | Horiba et al. | 364/413.19 |
| 4,812,983 | 3/1989 | Gullberg et al. | 364/413.17 |
| 4,894,775 | 1/1990 | Kritchman et al. | 364/413.16 |
| 4,979,111 | 12/1990 | Nishimura | 364/413.16 |
| 5,051,904 | 9/1991 | Griffith | 364/413.16 |
| 5,099,846 | 3/1992 | Hardy | 364/413.13 |

FOREIGN PATENT DOCUMENTS

| | | |
|---|---|---|
| 0083455 | 7/1983 | European Pat. Off. |
| 0089096 | 9/1983 | European Pat. Off. |
| 3604375 | 8/1986 | Fed. Rep. of Germany |
| 2536862 | 6/1984 | France |

OTHER PUBLICATIONS

R. G. Waggener, et al., "Hybrid reconstruction algorithm for x-ray computed tomography", 16 Med. Phys. (1989).

M. Hamron (Ed.), "Simulator as 'Mini-CT' treatment control," CART News No. 8 (1987).

C. Perez and L. Brady, "Principles in radiologic physics, densimetry, and treatment planning," in Principles and Practice of Radiation Oncology, Philadelphia: J. B. Lippencott Co. (1987).

H. Peng and H. Stark, Direct Fourier reconstruction in fan beam tomography, MI-6 IEEE Transactions on Medical Imaging 209-219 (1987).

G. Kowalski, "Suppression of ring artifacts in CT fan beam scanners", NS-25 IEEE Transactions on Nuclear Science 1111-1116 (1978).

*Primary Examiner*—Roy N. Envall, Jr.
*Assistant Examiner*—Laura Brutmar
*Attorney, Agent, or Firm*—Vaden, Eickenroht, Thompson, Boulware & Feather

[57] ABSTRACT

Apparatus and method for mounting on an existing x-ray simulator and calculating a back projected computed tomographic image. The detector array is linear and outputs signals from the photodiodes mounted therein to a preprocessor for smoothing, correcting and filtering and subsequent processing to transform the signal from that produced by an x-ray originating from a fan beam source, e.g., in a polar coordinate system, into the signal which would have been produced by a detector in an array on which a parallel beam is incident on a Cartesian coordinate system. The transformed data is converted to a gray scale value for a picture element having a specific position in the Cartesian coordinate system and output to an appropriate display. Data is taken at each incremental angle as the beam source and detector array rotate around a target object.

The method of reconstructing this back projected image involves correcting and smoothing the output signals, scaling those corrected and smoothed signals, and convolving the scaled signals into data characterizing the ray which is incident on each individual detector element into the equivalent intensity data had the incident ray originated from a parallel beam source. Also provided are methods for correcting the data for incorrect detector reading and for displacement of the detector array resulting from the off-center rotation of either or both of the x-ray source or the detector array.

14 Claims, 4 Drawing Sheets

METHOD AND APPARATUS FOR COMPUTING TOMOGRAPHIC SCANS

This application is a divisional of co-pending application Ser. No. 07/391,252, filed Aug. 9, 1989, now U.S. Pat. No. 5,128,864.

BACKGROUND OF THE INVENTION

1. Field of the Invention

The present invention pertains generally to the use of a detachable x-ray detector array in combination with an existing radiation therapy x-ray simulator to produce computed tomographic image reconstructions More particularly, the present invention relates to an apparatus for producing a computed tomographic scan from the width-collimated fan beam produced by an existing x-ray simulator and to a method for transforming the data produced by the detector array of the apparatus into a back projected image of the target object.

2. Introduction

X-ray computed tomography (CT) is a technique for obtaining crosssectional reconstructions of three dimensional objects using x-rays. In the simplest example of CT imaging, a narrow beam of penetrating x-rays is scanned across an object or patient in synchrony with a radiation detector on the opposite side of the patient. If the beam is monoenergetic or nearly so, the transmission of x-rays through the patient is given by the equation $$I = I_0 exp(-\mu x) \quad [1]$$

where the patient is assumed to be a homogeneous medium with the attenuation coefficient $\mu$. If the x-ray beam is intercepted by two regions with attenuation coefficients $\mu_1$ and $\mu_2$ and thicknesses $x_1$ and $x_2$, the x-ray transmission is characterized as $$I = I_0 exp[-(\mu_1 x_1 + \mu_2 x_2)] \quad [2]$$

This formula is generalized to many (n) regions with different linear attenuation coefficients with the argument of the exponent $$\sum_{i=1}^{n} \mu_i x_i = (\mu_1 x_1 + \mu_2 x_2 + \ldots \mu_n x_n) \quad [3]$$

$$I = \sum_{i=1}^{n} I_0 exp[-(\mu_i x_i)] \quad [4]$$

Separate attenuation coefficients cannot be determined with a single transmission measurement because there are too many unknown values of $\mu_i$ in the equation. However, with multiple transmission measurements at different orientations of the x-ray source and detector, the separate coefficients can be distinguished so that a cross-sectional display of coefficients is obtained across the plane of transmission measurements. By assigning gray levels to different ranges of attenuation coefficients, a display is obtained that represents various structures in the patient with different x-ray attenuation characteristics. This gray scale display of attenuation coefficients constitutes a CT image.

The first CT systems were introduced in approximately 1971 by the EMI Corporation of England for use in medicine. These early systems used an x-ray source mounted in a gantry with detectors. The patient was inserted between the x-ray source and the detectors and the joined x-ray source and detectors were moved about the patient to obtain projection rays through the patient. These values were fed to a computer which then reconstructed a cross sectional image of the plane through which the pencil beam of x-rays passed. During this translational scan of perhaps 40 cm in length, multiple (e.g., 160) measurements of the x-ray transmission were obtained. Next, the angular orientation of the scanning device was incremented one degree and a second translational scan of 160 transmission measurements was performed. This process of translational scanning at one degree increments was repeated through an arc of 180 degrees so that 28,800 x-ray transmission measurements were accumulated. Those measurements were then transmitted to a computer equipped with a mathematical algorithm for reconstructing an image of attenuation coefficients across the anatomical plane defined by the scanning x-ray beam.

Although this approach yielded satisfactory images of stationary objects, considerable time (4–5 minutes) was required for data accumulation and the images were subject to motion blurring. Soon after the introduction of pencil beam scanners, fan-shaped x-ray beams were introduced so that multiple measurements of x-ray transmission could be made simultaneously. Fan beam geometries, with increments of a few degrees for the different angular orientations (e,g., a 30-degree fan beam and 10-degree angular increments), reduced the scan time to 20–60 seconds and improved the image quality by reducing the effects of motion. Computed tomographic scanners with x-ray fan beam geometries and multiple radiation detectors constituted the second generation of CT scanners.

In late 1975, the third generation of CT scanner was introduced. These scanners eliminated the translational motion of previous scanners, using rotational motion of the x-ray tube and detector array or rotational motion of the x-ray tube within a stationary circular array of 600 or more detectors. With these scanners, data accumulation times as fast as two seconds are achievable.

Both stationary and rotating anode x-ray tubes are used in CT scanners. Many of the translation-rotation CT scanners have an oil-cooled, stationary anode x-ray tube with a focal spot on the order of $2 \times 16$ mm. The limited output of these x-ray tubes necessitates a sampling time of about 5 msec for each measurement of x-ray transmission. This sampling time, together with the time required to move and rotate the source and detector, limits the speed with which data can be accumulated with CT units using translational and rotational motion.

To reduce the sampling time of 2–3 msec, most fast-scan CT units use rotating-anode x-ray tubes, often with a pulsed x-ray beam, to achieve higher x-ray outputs. Even with rotating-anode tubes, the heat-storage capacity of the anode may be exceeded if cooling periods are not observed between sets of successive images.

After transmission through the patient, the x-ray beam is collimated to confine the transmission to a slice with a thickness of a few millimeters and to reduce scattered radiation to less than one percent (1%) of the primary beam intensity. The height of the collimator defines the thickness of the CT slice. This height, when combined with the area of a single picture element (pixel) in the display, defines the three-dimensional volume element (voxel) in the patient corresponding to the two-dimensional pixel of the display. A voxel encompassing a boundary between two tissue structures (e.g., muscle and bone) yields an attenuation coefficient for the pixel that is intermediate between the values for the two structures. This "partial volume artifact" may be reduced by narrowing the collimator to yield thinner slices. However, this approach reduces the intensity of the x-rays incident upon the detector and the detector signals are subject to greater statistical fluctuations, thus introducing more noise into the displayed image.

To reduce the detector response time, all detectors used in CT scanning are operated in current rather than pulse mode. Also, rejection of scattered radiation is assigned to the detector collimator rather than to pulse height analyzers. Detectors for CT scanning are chosen on the basis of detection efficiency (greater than 50%), short response time and stability of operation, and are either gas-filled ionization chambers or solid scintillation detectors. Scintillation detectors include NaI (TI) and CsI crystals and newer bismuth germanate (BiGeO) detectors chosen for their high detection efficiency and low fluorescence decay time. On information and belief, most ionization chambers in current use contain xenon pressurized up to 25 atm to improve the x-ray detection efficiency. With any detector, the stability of response from one transmission measurement to the next is essential for the production of artifact-free reconstruction images. With a pure rotational source and detector geometry, for example, detector instability gives rise to ring-shaped artifacts in the image. Minimum energy dependence of the detectors over the energy range for the CT x-ray beam also is important if corrections for beam hardening are to be applicable to all patient sizes and configurations.

All of the early CT systems were designed and built only to perform CT studies. The concept of using other types of radiation sources that had not been specifically designed for CT imaging was initiated in the mid 1970's.

Several of these efforts utilized existing x-ray therapy simulators. An x-ray simulator is a device that duplicates a radiation treatment unit in terms of its geometric, mechanical and optical properties, but uses a diagnostic x-ray tube as the source of radiation to simulate the properties of the treatment beam. A simulator allows the beam direction and the treatment fields to be determined while encompassing the target object with the simulator's irradiation. Since the simulator's emissions are generally less intense and less energetic than the emissions of therapy devices, there is a reduction in the target object's exposure to radiation.

The combination of a detector system and an x-ray therapy simulator provides the necessary front end of a CT system. Application of the requisite information processing techniques and algorithmic reconstruction processes in combination with the simulator cum detector system enable production of CT images.

Reconstruction Algorithm

The numbers computed by the reconstruction algorithm are not exact values of attention coefficients. Instead, they are integers, termed CT numbers, which are related to attenuation coefficients. On most newer CT units, the CT numbers range from $-1,000$ for air to $+1000$ for bone, with the CT number of water set at 0. CT numbers normalized in this manner are termed Hounsfield units and provide a range of several CT numbers for a one percent (1%) change in attenuation coefficient.

To portray the CT numbers as a gray scale visual display, a storage oscilloscope or television monitor may be used. This viewing device contains a contrast enhancement feature that superimposes the shades of gray available in the display device (i.e., the dynamic range of the display) over the range of CT numbers of diagnostic interest. Control of image contrast with the contrast enhancement feature is essential in x-ray computed tomography because the electron density, and therefore the x-ray attenuation, are remarkedly similar for most tissues of diagnostic interest. These electron densities vary from $3.07 \times 10^{23}$ elec/cc for fat tissue to $5.59 \times 10^{23}$ elec/cc for the densest tissue, bone. Lung tissue has a much lower electron density, $0.83 \times 10^{23}$ elec/cc, because of the alveolar and branchial spaces.

Known reconstruction algorithms are one of four types:

(1) simple back projection—In this method, each x-ray transmission path through the body is divided into equally spaced elements, and each element is assumed to contribute equally to the total attenuation along the x-ray path. By summing the attenuation for each element over all x-ray paths that transect the element at different angular orientations, a final summed attenuation coefficient is determined for each element. When this coefficient is combined with the summed coefficients for all other elements in the anatomical section scanned by the x-ray beam, a composite image of attenuation coefficients is obtained. Although the simple back projection approach to reconstruction algorithms is straight forward, such an algorithm produces blurred images of sharp features in the target object.

(2) integral equations—This reconstruction algorithm uses a one dimensional integral equation for the reconstruction of a two-dimensional image. In the convolution method of using an integral equation, a deblurring function is combined (convolved) with the x-ray transmission data to remove most of the blurring before the data are back-projected. The most common deblurring function is a frequency filter that removes the high-frequency components of the x-ray transmission data. These components are responsible for most of the blurring in the composite image. One of the advantages of the convolution method of image reconstruction is that the image can be reconstructed while x-ray transmission data are being collected. The convolution method is the most popular reconstruction algorithm used today in computed tomography.

(3) Fourier transform—In this approach, the x-ray attenuation pattern at each angular orientation is separated into frequency components of various amplitudes, similar to the way a musical note can be divided into relative contributions of different frequencies. From these frequency components, the entire image is assembled in "frequency space" and then reconstructed by an inverse Fourier transform reconstruction process into a spatially correct image. For high-resolution images, the Fourier transform reconstruction process requires a computer of considerable capacity.

(4) series expansion—In this technique, variations of which are known as ART (algebraic reconstruction technique) and SIRT (simultaneous iterative reconstruction technique), x-ray attenuation data at one angular orientation are divided into equally spaced elements along each of several rays. These data are compared to similar data at a different angular orientation, and differences in x-ray attenuation at the two orientations are added equally to the appropriate elements. This process is repeated for all angular orientations, with a decreasing fraction of the attenuation differences added each time to insure convergence of the reconstruction data. In this method, all x-ray attenuation data must be available before the reconstruction process can begin.

While the various algorithms used for CT image reconstruction each have their own limitations, the quality of the overall procedure is dominated by the quantity and quality of the measured transmission data. The quantity of data is restricted by the specific scanner design and by limitations placed on time and computer resources. Phenomena which tend to degrade the quality of the measured data include:

a) Geometrical errors such as misalignment or motion of the scanning system or patient motion,
b) Instability of the x-ray source,
c) Statistical fluctuation of the measured signal,
d) Polychromaticity (non-monochromaticity) of the x-ray beam,
e) The finite dimensions of the scanning aperture,
f) Residual signal due to the time response function of the detector system (afterglow).

If, as a result of these factors, the projection values derived from the measured data do not adequately represent the line integrals of the linear attenuation coefficients within the slice being scanned, even the most perfect reconstruction algorithm will give rise to a distorted image. Each of these factors and the manner in which they are addressed in the case of the method of the present invention is set out in the following paragraphs.

Geometrical Error

The most practical approach to error introduced by scanner misalignment or motion lies in the construction and maintenance of the scanner itself, including periodic testing of the mechanical registration. Patient motion is less controllable but can usually be minimized by proper patient support and through the use of the fast (fan beam) scanner. If patient motion is monitored, such as through the use of a transducer arrangement or a laser beam reflection method, then data correction is feasible. The correction amounts to the shifting of data in the computer or can be done by altering the algorithm parameters which define the position of the data.

X-Ray Source Instability

The instability of the x-ray source is generally corrected for by adjusting the measured data in accordance with the signal measured by a reference detector. Another approach is to monitor the electronic parameters of the x-ray source, such as kVp and mA, and to make the corrections to the measured data from this information. The reference detector method, while not extremely sensitive to kilovoltage variations, is simpler and more easily utilized through electronic hardware. Computer correction in accordance with the present invention makes possible the use of lower cost x-ray power supplies and kVp monitoring to correct for changes in effective beam energy.

Statistical Fluctuation

Systemic error may arise in such forms as drift and gain variations in the detector system and associated electronics, or in the form of background or bias currents. If these variations can be monitored and quantified, corrections can be implemented through hardware circuitry or computer correction. If such correction is not feasible, this type of error becomes superimposed upon random error from such sources as photon statistics and electronic noise. Electronic noise is a function of the detector and associated electronics while factors affecting the number of photons which can be counted include: radiation source output, detector efficiency, source-detector geometry, scan time per measurement, transmission through the patient, and detector aperture size. Random error cannot be dealt with by software methods, but minimizing this type of error is a major consideration in the design of any scanner system.

Polychromatic Effects

Since flux-rate requirements based on statistical considerations for any reasonable scan time normally rule out the use of other sources of radiation, an x-ray tube is the only practical photon source for CT scanning. As a result, a spectral distribution of photons is involved rather than photons of a single energy. Since lower energy photons have higher attenuation coefficients than higher energy ones, the beam becomes progressively "harder" as it traverses an increasing patient thickness. A "harder" beam, having a lower effective attenuation coefficient than a "softer" one, introduces a degree of inconsistency into the measured data used for reconstruction. In the absence of compensation for this effect, e.g., utilizing a fixed length water bath or software corrections applied at the preprocessing stage, this effect leads to a distorted image characterized by a general increase in reconstruction coefficients from the center to the periphery of the cross-section.

The object of preprocessing the measured transmission data before reconstruction is to "linearize" the logarithm of the ratio of the incident to transmitted intensity. For a monoenergetic beam traversing a homogeneous medium, this logarithm is a linear function of increasing thickness, while for a polychromatic beam this function is no longer linear. If the characteristic attenuation of a particular incident x-ray beam by an increasing mass thickness of water is known and if it can safely be assumed that the materials encountered within the body have attenuation properties similar to those of water, the measured data can be corrected to an idealized monoenergetic (linear) response for some suitable energy. Since the corrected data is then logarithmically linear, that data can be utilized by the reconstruction algorithm to produce a spatially consistent image that is independent of patient size. This correction may also be implemented by assuming an average composition of tissue and bone instead of water for the various degrees of attenuation.

Finite Dimensions of Scanning Aperture

The qualities of resolution and image sharpness are closely associated with aperture size. Theoretical development of the reconstruction algorithms is based upon an infinite amount of infinitely thin transmission data which, in practice, is approximated by a finite number of transmission measurements of an x-ray beam of finite dimensions. The minimum aperture size is limited by photon statistics for a given x-ray output, geometry and scan speed.

The slit height, perpendicular to the linear motion of the scanner, acts to make the resultant reconstructed coefficient a type of average coefficient over many thin transverse planes. This average is not inconsistent with the assumption of infinitely thin rays since the theoretical development of these algorithms is limited to two dimensions. Distortions due to this vertical smearing are somewhat minimized because of the homogeneity of the human body over short vertical distances. In some respects, this smearing is advantageous in that a larger volume is considered in each cross-sectional slice, hence fewer slices need be reconstructed to include the entire volume of interest. However, in the interpretation of the two-dimensional reconstruction, the resultant coefficient need not pertain to only one type of tissue, especially for small structures and near boundaries. This necessity is particularly important in relating these coefficients to effective atomic number, density, chemical composition, or specific tumor types.

The slit width, parallel to the linear motion of the scanner, introduces a compromise between the algorithm development and practical measurement. The approximation that the average intensity transmitted along the width of the aperture is the same as the relative intensity along a central ray is partially responsible for the lack of sharpness noted along many boundaries and can significantly degrade resolution. If the slit width is less than the linear increment between samples, computer enhancement of the data is not feasible. However, if the slit width exceeds this increment, then information is available from which the intensity for an aperture of a width approaching that of the linear increment can be calculated in accordance with the present invention. This technique is comparable to reconvolving the point spread function from other imaging devices, except the correction is applied to the measured data before an image is formed rather than as a modulation transfer function enhancement done as a post processing procedure on the final reconstructed image. The deconvolution is along discrete steps, the measured data, and not a continuum, therefore leading to the limit of data resolution, the linear increment.

Time Response of Detector System

The time response is an important consideration in the choice of detector systems. If signal decay due to an impulse of radiation on a detector is slow, then it would appear from the measurements alone that some radiation was still incident on the detector some short time after radiation exposure. Likewise, a particular measurement during a scan may be partially due to radiation incident on the detector from some time prior to that measurement. In the case of the linear scanner considered here, this temporal smearing due to the detector response may be related to a type of spatial response of the detector by the time spacing of the measurements or scan speed. In this way, the time response of the detector is considered similar to or as part of the aperture transmission function and can be corrected for in the same manner.

Applicability to Fan Beam Scanners

For fan beam scanners, many of these correction techniques still apply. Furthermore, the temporal response of the detector is related to measurements made with the same detector as a function of angle (time). The aperture itself is less likely to overlap than in the case of the linear scanner, however, the effective aperture due to cross-talk and patient scatter may also be handled by these preprocessing techniques. Modifications applicable to patient scatter may include making a correction to the measurement of interest as a function of intensity attenuated (including scatter) rather than intensity transmitted to a nearby detector along with the distance of this detector from the detector of interest. In any case, this type of scatter correction is just an approximation. The corrections pertaining to geometrical errors, instability of the x-ray source and the polychromaticity of the x-ray beam are applicable to either type of scanner.

Some of these techniques are known to be in commercial use, especially in regard to polychromatic correction. Hardware approaches to some of the problems are also common, such as careful construction of the scanner and use of patient supports and restraints to minimize geometrical error, reference detector methods to compensate for x-ray source variation, temperature compensating amplifiers to reduce drift, increasing x-ray filtration to reduce polychromatic effect, increasing x-ray output to allow for smaller apertures, and the selection of detectors to reduce afterglow. Even so, the present method for reducing these factors which tend to degrade the quality of the data is beneficial and in some cases absolutely necessary.

Alternative approaches to the construction of CT systems involve combining radiation sources and detection systems and the mounting of permanent detection systems on linear accelerations (linac). These systems were developed to employ CT in patient positioning and as an aid in therapy planning, and utilized collimation of the linac output to produce a fan beam configuration in the CT system. Results with these systems can be made to coincide with other CT systems which use pencil beam geometry in the primary beam.

CT reconstruction has also been performed using a $CO^{60}$ teletherapy unit in conjunction with a GE Maxitron. In this application, rather than rotating the radiation source, the subject was rotated in front of the stationary radiation source to obtain the projection data for the cross-sectional reconstruction.

In spite of these many improvements and alternate approaches, there remains a need for improved methods for reducing the effect of these error factors on a back projected image, as well as for actually back projecting the image of the target object. There is also a need for an apparatus for implementing these methods, and especially an apparatus which is capable of being mounted in combination with an existing x-ray simulator without changing the function of that apparatus. Such an attachment makes possible a highly desirable economy and flexibility of application, especially when combined with the improved methods of correcting for the effect of the above-listed error factors and back projecting the image of the target object. It is, therefore, an object of the present invention to provide such an apparatus and such a method.

Another object of the present invention is to provide a method and apparatus which improves the resolution of a CT image by providing an improved method for back projecting that image.

Another object of the present invention is to provide an improved method for correcting for the errors in the calculated back projected image caused by off center rotation of the source of the x-ray beam and/or the detector array.

Other objects, and the advantages, of the present invention will be apparent to those skilled in the art from the following description of the presently preferred embodiments thereof.

SUMMARY OF THE INVENTION

These objects are achieved by providing an apparatus for back projecting a CT scan comprising a linear detector array, the mounting of which is adapted for mounting to the film holder of an x-ray simulator normal to the central axis of the fan beam produced by the simulator without altering the original function of the x-ray source of the simulator, which comprises a plurality of individual radiation detector elements. Each individual detector element produces an output signal having an amplitude proportional to the energy intensity of an x-ray incident thereon, the intensity of an incident x-ray being proportional to the density of the target through which the incident x-ray passes before striking the individual detector element. Also provided is means for collecting the output signals of each individual detector element at a plurality of incremental angles as said detector array and the source of the fan beam are rotated around the target object and translating said signals into a back projected computer tomographic scan of the target object.

Translation is accomplished by correcting for the spread of the x-rays in the fan beam and for the differences in the intensity of the x-rays comprising the fan beam depending on the position of the individual detector element in the detector array relative to the central axis of the fan beam. Translation also involves scaling the output signal to account both for the relative distance from the source of the fan beam to the target object and for the distance from the source of the fan beam to the detector array and transforming the output signal from each detector element into an output signal representing the output signal that would have been produced by each detector element had the incident x-ray originated from a parallel beam instead of a fan beam. Finally, translation involves converting the transformed output signal at each incremental angle of the detector array into a gray scale value for a picture element having a specific set of coordinates relative to the coordinates of the detector array and outputting the gray scale value to an appropriate display means for displaying the tomographic scan.

Also provided is a method of producing a computed tomographic scan of a target object with an x-ray simulator comprising the steps of projecting an x-ray beam through a target object, detecting the x-ray beam incident on a detector positioned on the other side of the target from the source of the x-ray beam, defining polar and cartesian coordinate systems to describe the geometry of the x-ray beam, target object, and detector and locating the position of the source of the x-ray beam, the center of rotation axis, and the detector on the polar and cartesian coordinate systems for each incremental angle as the source of the x-ray beam and the detector rotate relative to the center axis of the target object. The output signal from each detector is then transformed into an output signal representing the output signal which would have been produced by that detector had the incident x-ray originated from a parallel beam source rather than a fan beam x-ray source and the transformed output signal is converted at each incremental angle of the detector into a gray scale value for a picture element having a specific position on the cartesian coordinate system. The gray scale values are then output to an appropriate display device.

DETAILED DESCRIPTION OF THE PREFERRED EMBODIMENTS

Figure 1:
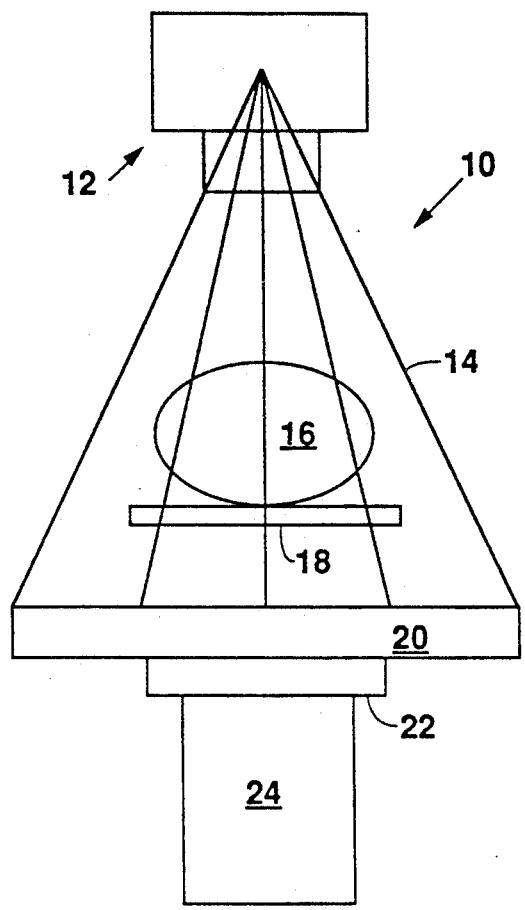
FIG. 1 is a schematic, sectional view of an x-ray simulator having an apparatus constructed in accordance with the present invention mounted thereto.

Referring to FIG. 1, there is shown a schematic representation of an x-ray simulator, indicated generally at reference numeral 10. X-ray simulator 10 is generally comprised of the x-ray tube 12 used for radiation therapy simulation which produces a fan beam, indicated at reference numeral 14, incident upon a target object 16 positioned on table 18. X-ray beam 14 is also incident upon the detector array (not shown) of the apparatus 20 of the present invention. The apparatus 20 is comprised of the linear detector array (see FIG. 2), the mounting of which is adapted for fitting into, mounting next to, or covering the film holder 22 of x-ray simulator 10 normal to the central axis of the fan beam 14 produced by the source 12 without altering the original function of simulator 10. The film holder 22, or cradle, is mounted on top of the image intensifier tube 24. The x-ray beam is collimated by using the shutters or collimators (not shown) provided by the x-ray therapy simulator 10. The beam is preferably shaped with a width of approximately one centimeter and a spread determined by the length of the detector array of the apparatus 20 of the present invention. If the projected shadow of the target object 16 to be scanned is less than the maximum width of the detector array, the length of the beam is decreased so as to just encompass the diameter of the target object 16.

Figure 2:
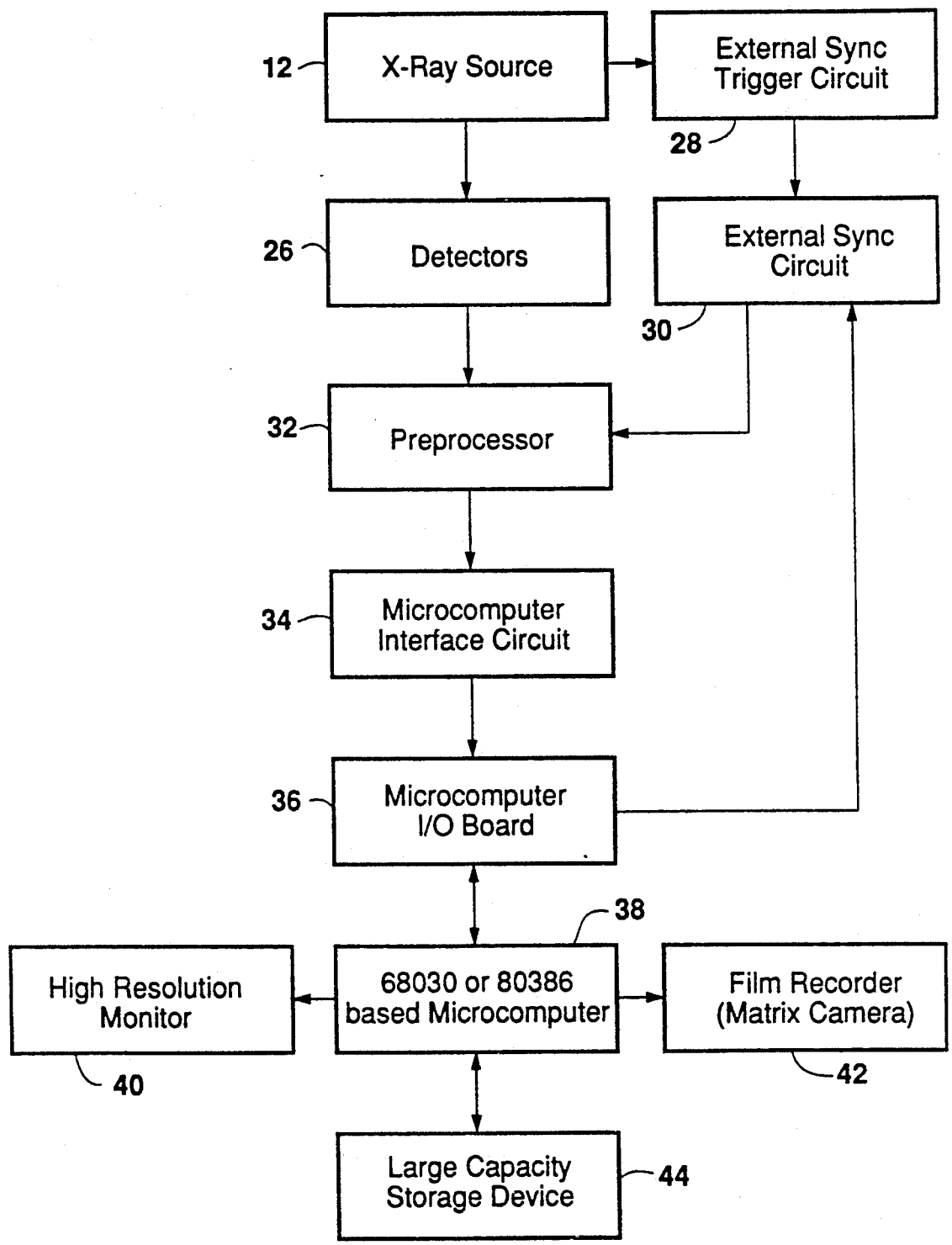
FIG. 2 is a schematic figure representing the interconnection of the component parts of the apparatus of the present invention and the processing of the data by those parts.

Referring now to FIG. 2, there is shown a schematic representation of an exemplary apparatus used in connection with the practice of the method of the present invention. The detector array 26 utilizes an image intensifying screen (not shown) placed over a linear photodiode array of detectors. In a presently preferred embodiment, the photodiode array 26 is comprised of eight to sixteen light sensitive modules (not shown), each composed of a silicone chip with 127 photodiodes (not shown). The photodiodes are used in a capacitive storage mode (with reverse bias) so that the light emitted by the intensifying screen discharges the photodiode capacitors. The scintillator material used is ytterbium-gadolinium oxide, a screen material commonly used in diagnostic radiology. Other scintillator materials may likewise be used to advantage in accordance with the method and apparatus of the present invention. This screen may also be made of different thicknesses to improve photon collection efficiency.

An external sync trigger circuit 28 is provided for interfacing the x-ray simulator 10 with an external sync circuit 30 to trigger the timing circuitry of the apparatus 20 of the present invention when the x-ray tube 12 starts to emit the fan beam 14. External sync circuit 30 provides the synchronization signal to the preprocessor 32 and determines the integration period of the detector array 26. The external sync circuit 30 consists of an input (not shown) to provide software control of offset and gain calibration reset signals to the preprocessor 32, a continuous clock circuit (also not shown) to provide the synchronization and integration period for the detector array 26 during gain calibrations, and a variable clock circuit (also not shown) which utilizes an EPROM to provide the synchronization and integration period for detector array 26 during data acquisition. Preprocessor 32 receives the analog signal from the detector array 26 and, under control of the external sync circuitry 30, digitizes the data and outputs the data to the microcomputer interface circuit 34.

Computer interface circuit 34 converts the data received from the preprocessor 32 to a format that is compatible with the input-output (I/O) board 36 of the particular microcomputer utilized for processing of the data as described below. The microcomputer I/O board 36, after receiving the data from microcomputer interface circuit 34, inputs the data to the memory of the microprocessor 38, which is preferably a 68030 or 80386-based microcomputer. In a presently preferred embodiment, an Apple Mac II Plus (tm) with eight megabyte memory, large hard disk, 80-140 megabytes, floppy disk and CRT displaying a 480×512 pixel image (or, alternatively, a special CRT to display a 512×512 image) having a 25 and preferably 30 megahertz internal clock is used to advantage. In addition, the output of the microcomputer I/O board 36 provides the software control signals to the external sync circuit 30 for offset and gain calibrations, the continuous clock and variable clock circuits. The microcomputer 38 performs the data manipulation routines described below to produce the CT image, outputting the processed data to an appropriate display means such as the high resolution monitor which provides a gray scale or color display of the reconstructed CT image, the film recorder (matrix camera) 42 which provides a hard copy output (film) of the image on the high resolution monitor 40, and/or the large capacity storage device 44 which stores the image data as well as patient information.

Figure 3:
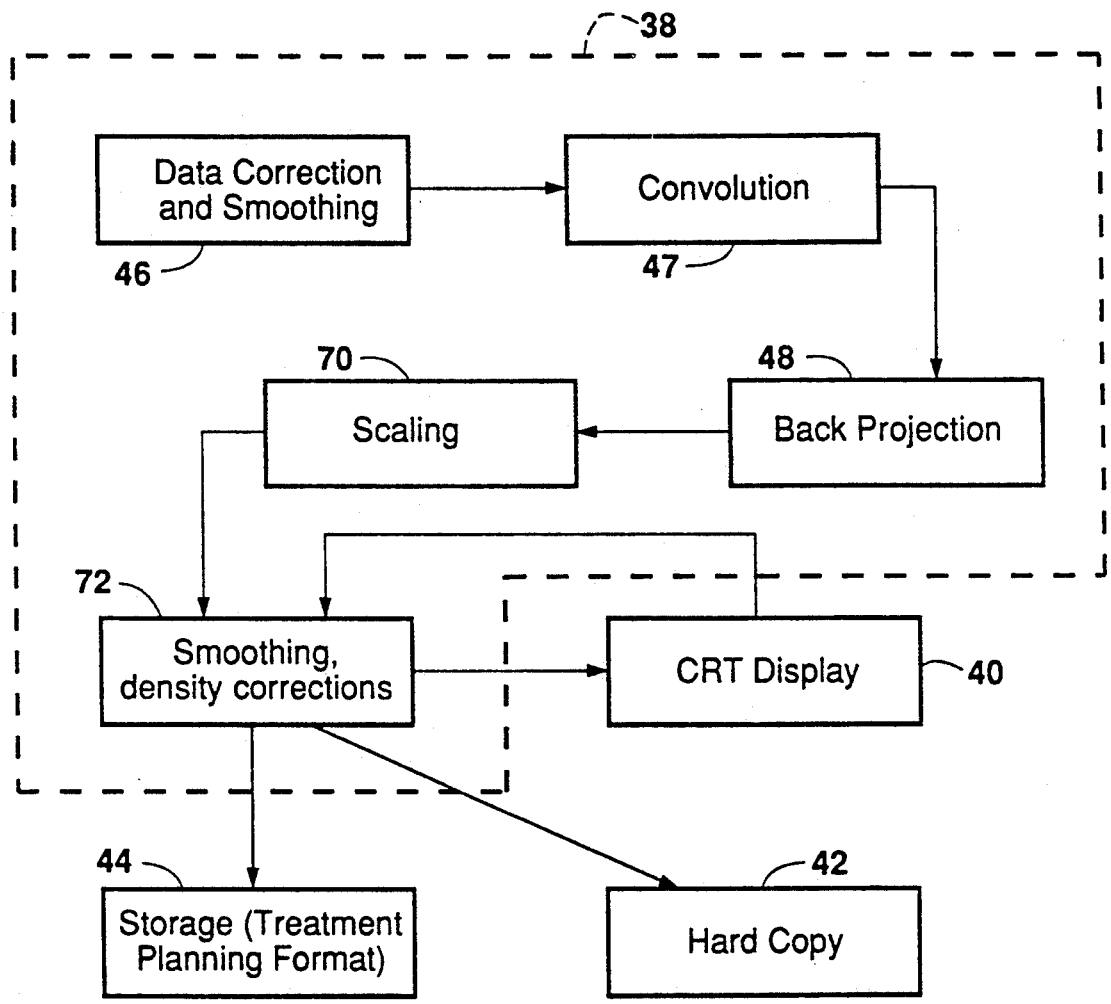
FIG. 3 is a flow chart of the processing of the data in accordance with the method of the present invention.

A general schematic outline of the data manipulation process is set out in FIG. 3. By the term "data" it will be understood that reference is made to the processed output signals of each individual detector or photodiode comprising detector array 26, which is proportional to the intensity of the x-ray incident thereon. Preprocessor 32 integrates the output signal of each photodiode and reads out the resultant signal upon external command controlled by microcomputer 38. In so doing, the data is corrected, smoothed, and filtered as shown in the step represented by box 46 in FIG. 3. This filtering step is required because the individual detector elements, or photodiodes, become defective and may malfunction either partially or completely. A correction algorithm is provided which identifies those faulty detector elements through comparison with the neighboring detector elements, the narrow separation between detector elements utilizes allow the generalization that the responses for adjacent detector elements should be relatively close to each other, and replaces the bad data with a corrected, interpolated value. A smoothing algorithm is provided for extending this method by setting a limit, or preset selection criterion, on the variation of adjacent individual detector elements and interpolating response values for those detector elements whose variation from the neighboring detector elements exceeds that preselected criterion. Recognition of when an individual detector element malfunctions is determined experimentally by exposure to x-rays both in air and through a phantom target (not shown) and the history of the detector array.

Characterizing each step in more detail, the data is first smoothed in accordance with the formula $$P(2) = (P(1) + P(3))/2 \qquad [5]$$

where $P(1)$, $P(2)$, and $P(3)$ represent the signal outputs from each of three successive detector elements in detector array 26. The smoothing is extended by selecting a maximum variation between adjacent detectors based upon the detector response history. For example, a cutoff limit of ±0.2 or 0.3 times the adjacent value may be selected so that if the reading from a particular detector element varies from its neighbors by more than 0.2 or 0.3 times the output of the neighboring elements, that output signal is replaced by the average of the output signal from the neighboring elements on either side of the bad element. In the event that several detectors in a row have malfunctioned, a scaled averaging method is used to correct the data. The difference between the last good output signal at one end of the malfunctioning row of detector elements and the first good output signal at the other end is divided by the number of detector elements malfunctioning and the resultant quotient is used as a constant which is sequentially and iteratively added to the last good output signal to provide a replacement for the next output. The correction is added to this value for the next reading and so on, up to the first good output signal. For example, given the following output signals, 110, 125, 255, 255, 255, 255, 140, 141, the correction is applied as follows:

$$C = (140 - 125)/5 = 3$$

In this example, there are five intervals from the last good output signal at one end of the malfunctioning detector elements and the first good output signal on the other end of the malfunctioning detector elements. The corrected output data is 110, 125, 128, 131, 134, 137, 140, 141.

Other corrections account for variations in x-ray output. These variations can be caused by current and/or voltage variations. Metering circuits on the x-ray simulator 10 are used to monitor these parameters, and the output of those circuits is used as an input to preprocessor 32. Current variations are corrected in linear fashion: if, for instance, the current drops from 5 mA to 4 mA, the detector elements are corrected as (5/4) x P(i). Voltage corrections are non-linear. The correction factor is formed as a power function of the voltage, i.e., $V^N$, where N is a number in the range $1.5 \leq N \leq 3$. N is determined experimentally and is idiosyncratic to the system being controlled. Suppose the voltage drops from 120 V to 110 V and, for that range, it has been determined that N=2. The correction is made as follows:

$$P(I)_{corr} = [120/110]^2 \times P(I) \qquad [5]$$

Additional corrections are performed using interpolation procedures to optimize accuracy in the calculated intensities used in back projection when correlating the detector in the detector array 26 that intercepts a back projected, or parallel beam, ray 50 which passes closest to the point in the target object 16 being reconstructed. The coordinate system in the back projection process is defined from i=0 at the first (−x) detector to $N_D-1$, where $N_D$ is the number of detectors. For example, using a 2048 detector array 20 with a detector spacing of δi=0.045 cm, the total length $D_L$ of the line of detectors in detector array 20 is $$D_L = 2048 \times 0.045 \text{ cm} = 92.16 \text{ cm}.$$

The factor 2048 is used because the detector line is based on the spacing of the individual detectors and there are 2047 spaces between the 2048 individual detectors in detector array 20. The center of the detector line is taken as zero. The x coordinate along this line then varies from $$-92.16/2 \text{ to } 92.16/2.$$

The x coordinate of the $i^{th}$ detector is $$x_i = (-46.08 \text{ cm} + (i+0.5)) \times (0.045 \text{ cm}),$$

e.g., for the $1135^{th}$ detector, $$x_{1135} = (-46.08 + (1135 + 0.5)) \times (0.045) = 5.0175 \text{ cm}$$

The coordinate on the detector line where the ray passes closest to the reconstruction target point is designated $L_{bp}$ (back projected). Once this coordinate is determined, it is possible to calculate which individual detector will receive the ray passing through $L_{bp}$. Let $$N_{bp} = [(L_{bp} + 46.08)/\delta i) + 0.5] \qquad [6]$$

and $N_{bp} = \text{INT}[N_{bp}]$ where "INT[]" indicates the integer of the number in the brackets in equation [6] and the factor 0.5 is an end correction such that in the limit where $L_{bp}$ is approximately equal to −46.08, the formula will return the integer value of one (1).

Round off error in calculating this integer is minimized by linear interpolation. The fractional part of $N_{bp}$ is $$\text{INT}[N_{bp}] - N_{bp} = f_{bp}. \qquad [7]$$

In the simplest round off, i.e., if $f_{bp}<0.5$, $N_{bp}=\text{INT}[N_{bp}]$. If $f_{bp}\leq 0.5$, $N_{bp}=\text{INT}[N_{bp}]+1$. For example, if $N_{bp}=756.528$, the detector output taken would be P1(757). To be more exact, interpolation yields $$P1 = (1 - f_{bp}) P1([N_{bp}]) + f_{bp} P1([N_{bp}] + 1).$$

In the numerical example, P1 = (1−0.528) P1(756) + 0.528 P1(757).

The term 37 smoothing" (steps 46 and/or 72 of FIG. 3) refers to the filtering of the data by both smoothing and ripple filtering. Smoothing is accomplished using a set of reconstructed values which may be represented as $$\begin{array}{l} M(1,1) \; M(1,2) \; M(1,3) \ldots M(1,N) \\ M(2,1) \; M(2,2) \; M(2,3) \ldots M(2,N) \\ M(3,1) \; M(3,2) \; M(3,3) \ldots M(3,N) \\ \vdots \\ M(N,1) \; M(N,2) \; M(N,3) \ldots M(N,N) \end{array} \qquad [8]$$

Here, $N=2^k$ where k=an integer, i.e., N=128, 256, 512, etc. For four point smoothing for nearest neighbor (j denotes the row and i denotes the column):

$$M'(j,i) = [M(j-1,i) + M(j+1,i) + M(j,i-1) + M(j,i+1)]/4 \qquad [9A]$$

The top, bottom, and adjacent left and right neighbors are used with equal weight. For five point smoothing for nearest neighbor $$M'(j,i) = [M(j,i) + M(j-1,i) + M(j+1,i) + M(j,i-1) + M(j,i+1)]/5 \qquad [9B]$$

M(j,i) is added in along with the four nearest neighbors. For weighted neighbor smoothing with the central value given the greatest weight, nine point smoothing is used:

$$M'(j,i) = [1 \times M(j-1,i-1) + 2 \times M(j-1,i) + 1 \times M(j-1,i+1) + 2 \times M(j,i-1) + 4 \times M(j,i) + 2 \times M(j,i+1) + 1 \times M(j+1,i-1) + 2 \times M(j+1,i) + 1 \times M(j+1,i+1)]/16. \qquad [9C]$$

This weighting system can be varied with different weights applied to different locations depending upon the circumstances as known to those skilled in the art.

Ripple filters are used to eliminate the wave introduced into the reconstruction by employing Fourier methods. The first step in application of such a filter is to obtain x-ray transmission values for a water (uniform target density) phantom. With known reconstructed CT values, these true values are compared to observed CT values. The ripple filter factor for each picture element is given by the true value/observed value. To achieve correction, the value for each picture element is multiplied by the filter factor.

There are many other different types of filters which may be used to advantage depending upon the circumstances as known to those skilled in the art who have benefit of this disclosure. Such filters might include, for instance, edge enhancement filters, high frequency suppression, bone enhancement filters, soft tissue enhancement filters, and so on.

Figure 4:
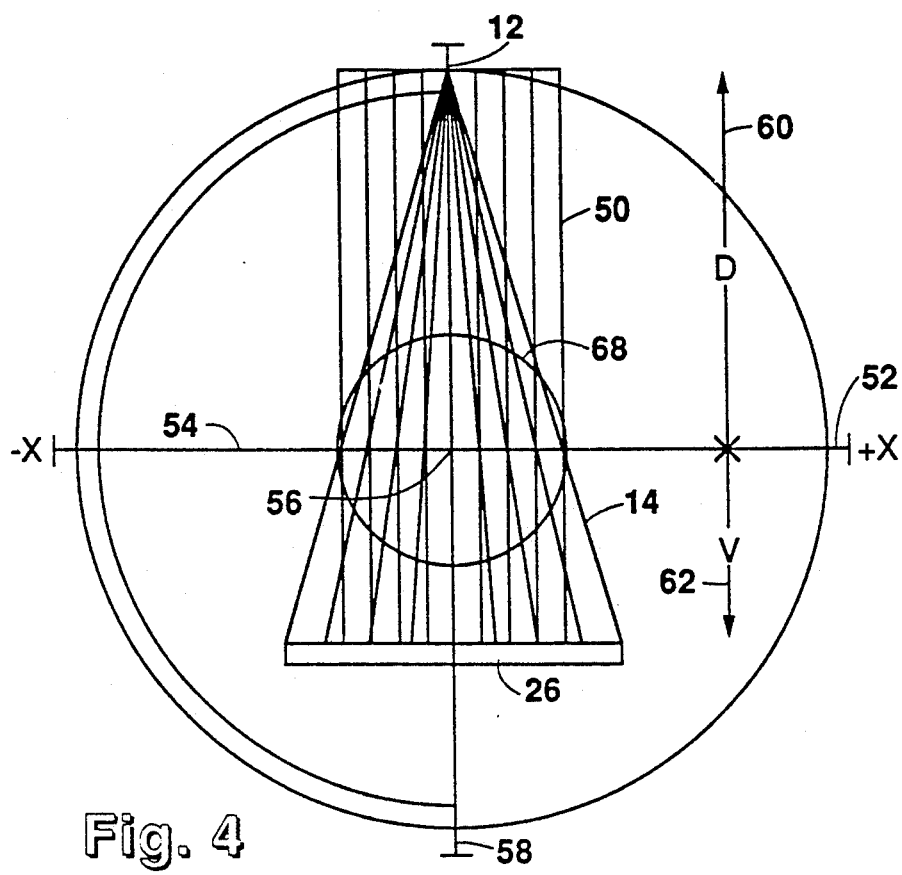
FIG. 4 is a schematic representation of the geometry of the coordinate system in which the x-ray source, target and detector array of the present invention are located.

The smoothed, corrected data from step 46 is convolved at step 47 and then back projected at step 48. Convolution 47 and back projection 48 are accomplished in accordance with an algorithm which is derived as follows. Referring to FIG. 4, there is shown the geometry for the fan beam 14, the parallel beam 50 and the coordinate system used to describe the algorithm of the present invention. In this system, x-axis 52 is on a line 54 through the center of rotation 56 and perpendicular to the y-axis 58 which passes IO through the center of rotation 56 on a line from the x-ray source 12 to the center of the detector array 26 which is parallel to the x-axis 52. The distance from the x-ray source 12 to the center of rotation 56 is D, reference numeral 60. The separation between the center of rotation 56 and the plane of the detector array 26 is a distance V, reference numeral 62. The x-ray source 12 and detector array 26 are incrementally rotated about the center of rotation 56 through angles T as shown at reference numeral 64 in FIG. 5. The increments may be equal in size or unequal. When equal increments are used, $T = 180°/N$ or $= 360°/N$, where N is the number of increments, and the system may be rotated either through a semi-circle or the entire arc of a circle.

The projection angle, $\delta T_j$, indicated at reference numeral 66, is given, in the equal increment case, by $$T_j = 90° + j\delta T \text{ where } 0 \leq j \leq N-1, \quad [10]$$

and $\delta T$ is the increment used to increase the proj angle. The x-ray source coordinates for each j are given by $$x_j = D \cos(T_j) \quad [11]$$

$$y_j = D \sin(t_j). \quad [12]$$

The angle, $T_0 = 90°$, defines the initial configuration of the system before rotation, e.g., at $j=0$. At this angle, $T_0$, the coordinates of each of the detectors in detector array 20 are:

$$x_d(0,i) = -D_L/2 + (i+0.5)\delta i \quad [13]$$

$$y_d(0,i) = -V \quad [14]$$

where $D_L$ = detector array length in cm., $\delta i = D_L/N_D$ detector spacing in cm., $N_d$ = number of detectors in the array, and $0 \leq i \leq N_D - 1$ The 0th detector is considered the left most (-y) in detector array 20. The spacing is actually the distance between the centers of each detector in detector array 20.

For $T_j > 90°$, the coordinates of each detector in detector array 20 are given by:

$$x_d(j,i) = x_d(0,i) \cos(j,\delta T) - y_d(0,i) \sin(j,\delta T) \quad [15]$$

$$y_d(j,i) = x_d(0,i) \sin(j,\delta T) + y_d(0,i) \cos(j,\delta T) \quad [16]$$

In FIG. 4, the parallel rays 50 are constructed by backprojection from the detector array 26. The intersections of the parallel 50 and fan beam 14 rays define the circle of reconstruction 68.

In defining the circle of reconstruction 68, the next step 70 (see FIG. 3) in manipulation of the data is accomplished by microprocessor 38 using the following steps. The diameter of the reconstruction circle 68, $D_{rc}$, along the line 54 is given by the scaling relationship, $$D_{rc}/D = D_L/W \quad [17]$$

where $W = D + V$ and is the distance from the source 12 to the center of detector array 26. The Jacobian of the scaling transformation from the line of the detector array 26 to the line 54 along the diameter of the reconstruction circle 68 is $$M_1 = D/(W). \quad [18]$$

The distance between successive back projected parallel beams or detector rays 50 at the level of the diameter of the reconstruction circle 68 is $$\delta \bar{i} = \delta i \, M_1. \quad [19]$$

The scaling factor $M_1$ allows transformation of the data taken along the detector line to appropriate values along the parallel line 54 through the center of rotation 56 and lying along a diameter of the reconstruction circle 68.

To normalize the projected data from the incident beam, fan beam projection data is taken for x-ray transmission through air and through target objects. Let $$p(j,i) = \log(r_{a(j,i)}/r_{p(j,i)}) \quad [20]$$

where $r_{a(j,i)}$ is the ith detector reading at angle j in air and $r_{p(j,i)}$ is the ith detector reading at angle j for x-rays transmitted through the patient or other target. The ranges of the integer indices are the same as defined above.

Figure 5:
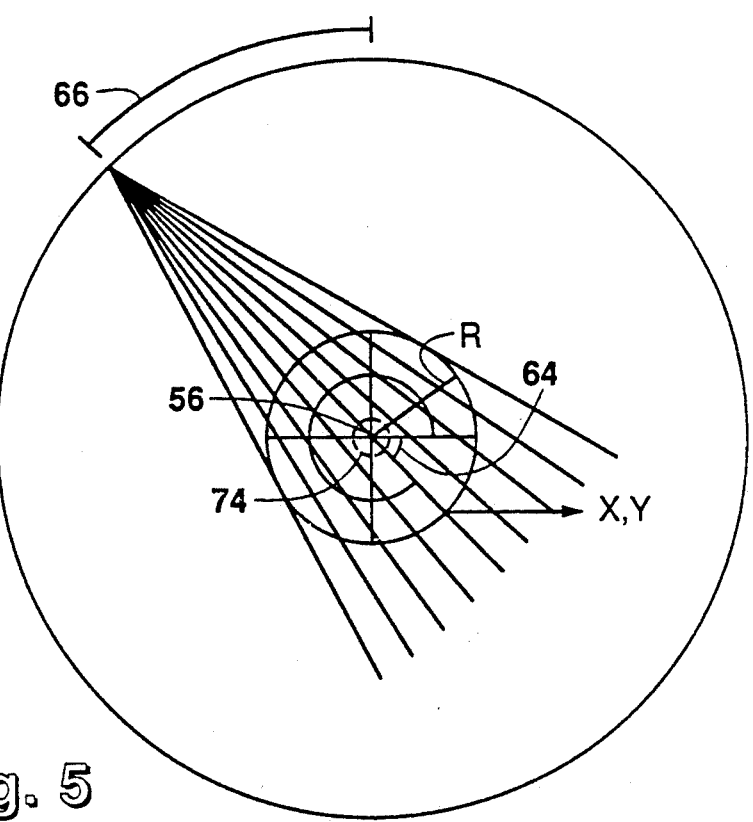
FIG. 5 is a schematic representation of the geometry of the back projected image computed in accordance with the method of the present invention.

For each angle $T_j$, the one dimensional discrete Fourier transform of the projection data are calculated as:

$$b[FT1(j, b)] = \sum_{i=0}^{N_D-1} p(j, i) \cos(2\pi b i / N_D) \quad [21]$$

$$c[FT2(j, c)] = \sum_{i=0}^{N_D-1} p(j, i) \sin(2\pi c i / N_d) \quad [22]$$

where b and c are the indices defining incremental distance in the horizontal and vertical dimensions, respectively, in the portion of the coordinate system in the circle of reconstruction 68 as more fully described in FIG. 5 and infra in connection with the discussion of equations [49] and [50], and $0 \leq b_i, c_i \leq N_D - 1$.

These transforms are multiplied by the ramp frequency filter. In the notation of discrete Fourier transformations, these are:

$$G1(j,b) = G1(j,N_b - b) = b[FT1(j,b)] \quad [23]$$

$$G2(j,c) = G2(j,N_c - c) = c[FT2(j,c)] \quad [24]$$

$$\text{where } 0 \leq b,c \leq N_{b,c} \quad [25]$$

$$\text{and } N_{b,c} = N_D/2 \text{ even}) \quad [26]$$

$$N_{b,c} = (N_D - 1)/2(N_D \text{ odd}). \quad [27]$$

The application of filters as outlined above is facilitated by working in the frequency domain. It is useful to modify the product transforms using spatial and frequency domain notation. Here, the step-wise, discrete functions G1(j,b) and G2(j,c) are rewritten as continuous functions, $$G1(j,f) = fFT1(j,f) \quad [28]$$

$$G2(j,f) = fFT2(j,f) \quad [29]$$

where, as before, $0 \leq j \leq N_D - 1$ and f, the frequency, is determined by the sampling theorem which states that where a function h(x) is defined over the range $2R_{rc}$ (diameter of the reconstruction circle 68) then the Fourier transform of h(x), H(F), is fully described by points $\delta F = \frac{1}{2}R_{rc}$ apart. Conversely, if the range of interest of H(F) is $2F_M$ then h(x) may be sampled at intervals not greater than $\delta i = \frac{1}{2}F_M$. Thus, in equations [28] and [29], $F = 0, F_1, F_2, \ldots F_M$, and $$F_M = 1/(2\delta F) \text{ Nyquist frequency, and} \quad [30]$$

$$F_M = \frac{1}{2}R_{rc} \text{ Nyquist frequency spacing} \quad [31]$$

The inverse Fourier transform of equations [23] and [24] may be performed to obtain the modified projection ray, P1(j,f) directly. However, this technique does not yield results as good as those obtained by utilizing the results of equation [36], infra.

The ramp frequency filter, $|f|$ (absolute value of f), appears as the Jacobian of the transformation from rectangular coordinates to polar coordinates. Equations [23] and [24] are the frequency domain counterparts of the convolution in the spatial domain of the two functions P(j,i) and H(j,i). The convolution theorem is used to obtain:

$$P1(j, i) = \sum_{i_1=0}^{N_D-1} P(j, i_1)H(j, i - i_1) \quad [32]$$

where
P1(j,i) = modified projection rays
P(j,i) = original projection ray values
H(j,i) = inverse Fourier transform of the ramp filter,
$0 \leq i \leq N_D - 1$ and
$0 \leq j \leq N_D - 1$.

The inverse Fourier transform of the ramp filter is given in R,f notation as:

$$S(R, f) = 2 \sum_{F=0}^{F_M} |f|\cos(2\pi Rf)\delta f \quad [33]$$

The sine term does not appear because the ramp filter is an even function in frequency space and the contributions from the negative and positive parts of the frequency spectrum account for the factor, two, multiplying the summation.

It is useful to treat the inverse transform of the ramp filter in the limit as a continuous function. This treatment is accomplished by using the integral rather than the discrete transform, or converting the summation in equation [33] to its integral analog $$S(R, f) = \int_{-F_M}^{F_M} |f|\exp[2\pi i Rf]df \quad [34]$$

where i is the imaginary square root of $-1$. The integral in equation [34] is a truncated version of the transform of the absolute filter function with cutoffs at $\pm F_M$. Consequently, no frequencies greater than $+F_M$ or less than $-F_M$ will be found in real (configuration) space in the function S(R,f) convolved with the projection data; i.e., no frequencies outside the $\pm F_M$ band will be found in the convolved projection data.

Integration by parts is used to solve this integral to obtain:

$$S(R,f) = 2F_M \sin(2\pi RF_M)/(2\pi R) + 2[\cos(2\pi RF_M) - 1]/(2\pi R)^2 \quad [35]$$

Equation [35] reduces to:

$$S(R,f) = 2F_M \sin(2\pi RF_M)/(\pi R) - \sin^2[\pi RF_M]/(\pi R)^2 \quad [36]$$

S(R,f) is convolved with the projection data, p(r,t) where t is the angle of the projection line with the +y axis 58 measured counter clockwise and R is the distance of the projection ray from the origin (see FIG. 5); thus $R = K\delta R$, where K is a general index defining the distance of the point in question from the origin of the coordinate system. Lower case letters, "p" and "t", are used to indicate variables in configuration space and capital letters are used to represent variables in frequency space. Accordingly, $$p1(R,t) = p(R,t) * S(R,) \quad [37]$$

where "*" denotes convolution.

The conceptual development leading to equation [37] is used to derive the hybrid reconstruction algorithm used in the method of the present invention. Returning to the discrete representation, the Fourier inverse transform of the ramp function, $|f|$ is written as:

$$S_{disc}(k) = [1/\delta i(F_M)^2] \sum_{-F_M}^{F_M} |f|[\exp(2\pi ifk/F_M) + \exp(-2\pi ifk/F_M)] \quad [38]$$

Again, $\delta i$ is the spacing in the detector array 26 or the distance between back-projected parallel rays 50, f denotes the frequency, and $F_M$ is interpreted here as the number of frequencies in the frequency band.

Since $|f|$ is an even function, equation [38] may be rewritten as:

$$S_{disc}(k) = [1/\delta i(F_M)^2] \sum_{f=0}^{F_M} f\cos(2\pi fk/F_M). \quad [39]$$

This simplification in equation [39] results from the fact that $|f|$ is an even function about the origin. The factor two results from changing the limits from $-F_M \leq F \leq F_M$ to $0 \leq F \leq F_M$ and is absorbed in the cosine definition.

When k=0, equation [39] becomes $$S_{disc}(0) = (F^2_M - 1)/(4\delta i F^2_M). \quad [40]$$

In the limit, as $F_M$ approaches $\infty$, equation [40] simplifies to $$S_{disc} = 1(4\delta i). \quad [41]$$

When k is different than zero, equation [39] becomes $$S_{disc} = \frac{(F_M - 1)\sin^2[\pi(F_M + 1)k/(2F_M)] - (F_M + 1)\sin^2[\pi(F_M - 1)k/2F_M]}{2F_M^2 \sin^2(kF_M)} \quad [42]$$

In the limit, as $F_M$ approaches $\infty$, the expression in equation [42] becomes:

$$\text{ti } S_{disc} = [-\sin^2(\pi k/2)]\delta i(\pi F^2_M)]. \quad [43]$$

When k is even and nonzero, $S_{disc} = 0$. When k is odd and nonzero, $$S_{disc} = -1[\delta i(\pi F_M)^2]. \quad [44]$$

Combining the conditions, the expression for $S_{disc}$ to be used in the convolution is $$S_{disc} = 1/(4\delta i) - 1/[\delta i(\pi F^2_M)]. \quad [45]$$

Equation [32] is rewritten as:

$$P1(j, i) = [P(j, i)/(4\delta i)] - [1/(\pi^2 \delta i)] \sum_{i_1=0}^{N_D-1} P(j, i_1)^2 \quad [46]$$

where $(i-i_1)$ is odd only. Equation [46] reduces in the real space convolution summation to:

$$P1(j, i) = [P(j, i)/(4\delta i)] - [1/(\pi^2 \delta i)] \sum_{i_1=0}^{N_D-1} P(j, i_1)/(1-i_1)^2, \quad [47]$$

where $(i,i_1)$ is odd only, and $0 \leq i \leq N_D-1$, $0 \leq j \leq N_D-1$. The $\delta i$ in the convolution summation has cancelled one $\delta i$ in the denominator of both the first and second terms of equations [46] and [47], while the first term is now entirely outside the summation. The odd only summation for $(i,i_1)$ is caused by the $\sin^2$ term being zero when $(i,i_1)$ is even and $+1$ when $(i,i_1)$ is odd.

Back projection geometry is shown in FIG. 5. The x,y increments are given by:

$$\delta x, \delta y = 2R_{rc}/N_p \quad [48]$$

where $N_p$ = number of pixels in one dimension, i.e., 32, 64, 128, etc. and $R_{rc}$ = radius of reconstruction circle 68:

$$x = -R_{rc} + (\delta R_{rc}/2) + b\delta R_{rc} \quad [49]$$

$$y = R_{rc} - (\delta R_{rc}/2) + c\delta R_{rc} \quad [50]$$

and $b, c = 0, 1, 2, \ldots N_P - 1$. $\quad [50]$

The linear coefficient for each x,y or b,c is:

$$\mu(b, c) = \sum_{i_5=0}^{N-1} P1(j, i_5(x, y))\delta T1, \quad [51]$$

where N = number of angle increments and $\delta T1$ is $\pi/N$ for both 180 and 360 degrees of rotation. Here, $i_5(x,y)$ is determined at each angle, and j is the number of the parallel ray 50 at the projection angle j which lies closest to the point x,y. The absorption coefficient is calculated from the following relations. The angle $\phi$ of the ray of interest is defined by:

$$\phi = \tan^{-1}(y, x). \quad [52]$$

Because $\phi$ is used in conjunction with $T_j$, $\phi$ must be defined in the same fashion as $T_j$, or from 0 to 360 degrees. If $x < 0$ and $y > 0$, then $90° \leq \phi \leq 180°$. If $x < 0$, and $y < 0$, then $180° \leq \phi \leq 270°$. If $x > 0$ and $y < 0$, then $270° \leq \phi \leq 360°$. Let $$L_8 = Wr_5 \sin\{[T_j - \phi]/[D - r_5 \cos(T_j - \phi)]\} \quad [53]$$

$$\text{where } r_5 = (x^2 + y^2)^{\frac{1}{2}} \quad [54]$$

$$\text{and } i_5(x,y) = INT[(L_8 + D_L/2)/i + 0.5]. \quad [55]$$

As before, "INT[]" is the "integar part of". The factor 0.5 appears in equation [55] because when $L_8 = -D/2$, s = -DL/2, $i_5(x,y)$ must be zero.

In the back projection process, a coordinate system is defined from $i = 0$ to $N_D - 1$ running from the lefthand $(-y)$ side of the detector line, $N_D$ is the number of detectors, and the detector array 26 is marked off in the same fashion as a meter stick. In the back projection process, the point along the detector line is determined where the parallel ray 50 passing closest to the point in the object 16 being reconstructed falls. This is $L_8$. With $L_8$ defined, the number of the detector corresponding to $L_8$ is determined. For example, suppose $L_8$ was calculated as 15.463 using equation [53] and assuming the detector array 26 is comprised of 2048 detectors and is of the length 92.16 cm as calculated above, the number of the detector lying on that point is given by $$i_5 = INT[(15.463 + 69.12/2)/0.045) + 0.5] = 1112.$$

This calculation indicates that the ray 50 from detector 1112 passed nearest the point (x,y) that is being reconstructed.

The quantity $L_8$ is defined differently for the hybrid reconstruction algorithm of the present invention than for the parallel beam geometry. At each angle, $T_j$, a line is passed from the x-ray target position $xT_j, yT_j$ through the point x,y and from there to an intersection with the x-ray detector line. Thus, $L_8$ is defined as the distance $\pm$ from the center of the detector line. For each value of x,y, there are N back projections.

In practice, a rectangular grid with $N_p \times N_p$ dimensions is reconstructed and all values of $\mu_{b,c}$ lying outside the circle of reconstruction 68 are set equal to zero. Using the rectangular grid for reconstruction greatly simplifies any smoothing routines when they are utilized. Further, interpolation may be used when a ray 50 does not pass through a point in the back projection.

Figure 6:
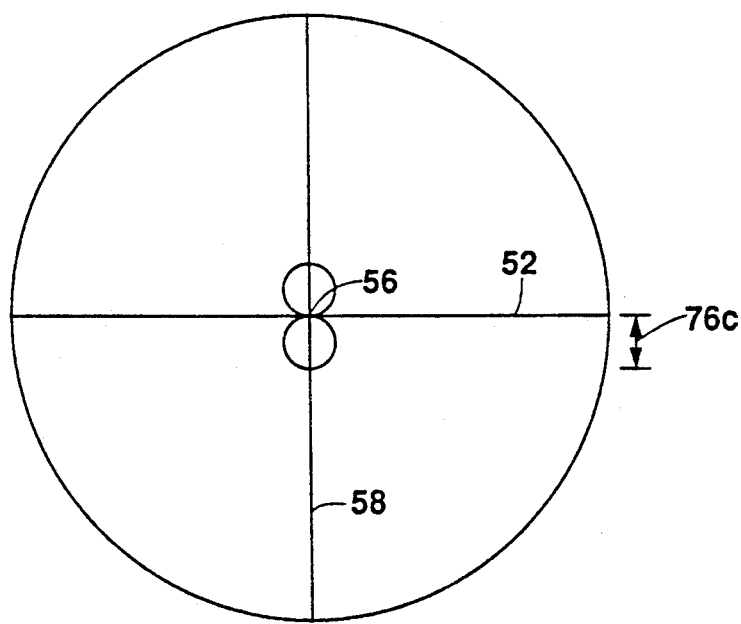
FIG. 6 is a graphical representation of an exaggeration of a measured center of rotation shift for an x-ray simulator rotating 360°. The off-center shift $S_j$ is plotted as a radius from the center versus the angle in degrees.

Referring now to FIG. 6, which is a graphical representation of an exaggeration of a measured center of rotation shift for an x-ray simulator rotating 360°, the off-center shift $S_j$ (shown at 76) is plotted as a radius from the center of rotation 56 versus the angle in degrees. When the x-ray beam which should fall on the central detector in the detector array 26 does not pass through the center of the circle of reconstruction 68, two errors may occur. The first error is a linear displacement of the detector array 26 parallel to the central axis of the fan beam 14. The second error is the magnification or demagnification of the distance between detector arrays ($\delta i$) used in the hybrid reconstruction algorithm described above. The latter error occurs when the center of rotation 56 is shifted in a direction perpendicular to the line on which the linear detector array 26 is positioned (e.g., the detector line). Further, both errors may occur at the same time.

Figure 7:
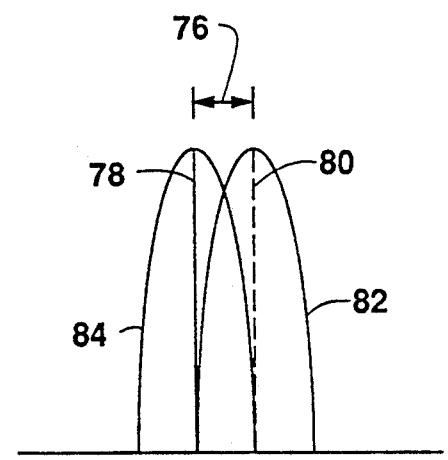
FIG. 7 is a graphical representation of a method for measuring the center of rotation shift as a function of an angle j.

Referring to FIG. 7, a simplified method of measuring the shift in the center of rotation is illustrated graphically. A round rod (represented schematically at reference numeral 74 in FIG. 5) which is relatively opaque to x-rays is placed at the nominal center of rotation shown by line 78 in FIG. 7, and data obtained using the method of the present invention is shown as curve 84. An eccentricity in the center of rotation causing a shift in the direction parallel to the central axis of the projected fan beam 14 results in projection data for the rod 74 with a center shown by the dotted line 80 with projection data 82. The curves 82 and 84 shown in FIG. 7 represent the reconstructed projection data taken over each angle $T_j$. From this data, the shift, shown at reference numeral 76 in FIGS. 6 and 7, in the number of detector widths for each angle is measured. This shift is used to correct equation [44] as follows:

$$i_5(x,y) = INT[(L_8 + D_L/2)/i - s_j + 0.5], \quad [56]$$

where $s_j$ is equal to the shift in number of detector widths. Magnification or demagnification of $\delta i$ is ignored. When the center of rotation shift is present, the geometry must be altered so that at the maximum shift in either direction, the shifted detector rays 50 at the edge of detector array 26 will still pass through the target object 16.

Having described a preferred method in accordance with the present invention, a method of conducting a CT scan using that method will now be described. Initially, eccentricities in the rotation of x-ray tube 12 must be determined and the individual detectors comprising detector array 26 calibrated. A kit (not shown) comprised of several rods in a holder, aluminum filters, and a CT phantom are provided for that purpose. Placing the center of the phantom for determining motion eccentricities at the nominal center of rotation 56, a scan is performed to identify any shift in the center of rotation 56. That scan also enables verification of the angle encoder output, whether that angle encoder (not shown) is integrated with the apparatus hardware (see FIG. 2) or output from those x-ray simulators which include such an encoder.

The aluminum filters are then used to determine the effective energies and x-ray output for the nominal operating voltage of the x-ray simulator. That data is used for correcting individual detector output at different voltages as at step 46. With a second phantom comprised of different materials, scans are performed at different voltages. The results are used to set up a Hounsfield scale for the different energies.

Once the initial measurements have been accomplished to load the correction algorithms into microcomputer 38 and the detectors of detector array 26 calibrated, the patient/target object 16 is positioned and the desired current and voltage parameters selected. The computer program is then initiated to acquire CT data, and on computer ready signal, x-ray output is initialized first and the x-ray rotation started. For $j=0$ to 359, where j is the angle in degrees, the computer is signaled to acquire data at approximately one degree intervals (or any other odd or even increments as selected by the operator). For $i=0$ to $N_D-1$, where ND is the number of detectors comprising detector array 26 and is operator selectable, PP(j,i) is acquired where PP(j,i) represents the output of the analog to digital converter (ADC) in microcomputer I/O board 36 for the detector i at the angle j. Note that the number of increments (angles) multiplied by the number of detectors will be the number of individual data points and that, for instance, where $0 \leq PP(j,i) \leq 4095$, 4095 corresponds to a 12 bit ADC, 8191 corresponds to a 13 bit ADC, 16,383 corresponds to a 14 bit ADC, and so on.

Each of the quantities PP(j,i) is then multiplied by a correction number obtained from the calibration procedure (step 46) to adjust the data to the values that would have been read if the individual detector was operating perfectly. This correction also remedies the beam hardening artifact as discussed above. A reference detector out is also used to correct for variation in the output of the x-ray unit as a function of the angle j.

PP(j,i) is the input to the hybrid reconstruction algorithm/convolution routine (steps 47 and 48), and after convolution, Fourier artifact filters are applied as described above. For $c=0$ to $b_p-1$ and $b=0$ to $N_p-1$, the back projection is done (step 48) and then repeated at the next b, next c.

Reconstructed linear attenuation coefficients are then converted to gray scale values using the Hounsfield scale derived from scanning the phantoms described above in connection with the setup procedures. A water phantom is scanned and the reconstructed coefficients are assigned 1000, with air being 0. Other values, such as for bone, are then automatically given a value in this scale. In this fashion, the Hounsfield scale is potentially wider than that of prior known CT scales, enabling detection of variations in CT values not currently available. By way of example, if the scan of a water phantom gives a value of 0.18 per cm for an average linear attenuation coefficient of water, 1000 is assigned as the value for water and $1000/0.18=555.55$ is obtained as the scale factor for the unit being used. As is known in the art, $0.36 \times 5555.55$, or 2000, is assigned a gray scale of 0 to represent the densest scale for this system, or twice the density of water, and $2000/255=7.843$ is the distribution of the gray scale number vs. CT numbers:

0 $CT$ $scale = air = 255$ $gray$ $scale$

1000 $CT$ $scale = water = 127$ $gray$ $scale$

2000 $CT$ $scale = twice$ $density$ $of$ $water = 0$ $gray$ $scale$

The CT values may be displayed along with gray scale numbers if desired.

Although described in terms of the above presently preferred embodiments, it is not intended that the scope of the invention be limited thereto. Instead, it is intended that changes in the specifics set out above which do not depart from the spirit of the invention described herein be included within the scope of the following claims.

What is claimed is:

1. A computed tomography apparatus comprising:
   - an x-ray radiation therapy simulator including a beam source for producing a width-collimated x-ray fan beam and a table supporting an object in the fan beam produced by the source so that the beam exposes substantially the entirety of the object;
   - a detector selectively mountable to said simulator at a location in the fan beam on the opposite side of the table from the beam source and which, when removed therefrom, does not alter the original function of said simulator;
   - said detector including a plurality of individual radiation detector elements mounted to said simulator on a line having an axis which is substantially perpendicular to the central axis of the fan beam, each of the detector elements producing an output signal having an amplitude proportional to the intensity of the radiation incident thereon;
   - said simulator including means for rotating the beam source together with said detector mounted thereto along a substantially circular arc about a center for taking a plurality of exposures of the object at angular increments along the circular arc; and
   - a computer operably connected to said detector programmed for receiving, storing, and processing the output signals of each of the detector elements at each angular increment, calculating the ratio of the output signals from radiation incident upon each of the detector elements traversing the object to the output signal from the same detector element for the same radiation in the absence of a target object, transforming the ratio into the frequency domain for filtering, and convolving the filtered signal to produce a value in the spatial domain representing the output signal of each detector element had the detector element detected a parallel beam of radiation from the source at each angular increment having a central axis which is contiguous and colinear with the central axis of the fan beam.

2. The apparatus of claim 1 wherein said detector means is mounted to the film holder of said x-ray simulator.

3. The apparatus of claim 1 additionally comprising an x-ray opaque rod for positioning on the table of the x-ray simulator for yielding projection data from which any shift in the center of rotation for each angular increment is calculated to correct the convolved value for each increment for errors caused when the central axis of the fan beam does not pass through the center of a circle of reconstruction defined by the intersection of the fan beam and the back projected parallel beam.

4. The apparatus of claim 1 additionally comprising means for correcting errors of linear displacement along said detector means so that a shifted, back projected parallel beam at the edge of said detector array passes through the target object.

5. The apparatus of claim 1 additionally comprising means for displaying an image comprised of picture elements, each picture element in the image representing a shade of gray assigned to the convolved value for each detector at each angular increment.

6. The apparatus of claim 1 wherein said detector array comprises a photodiode array.

7. The apparatus of claim 1 additionally comprising circuitry for triggering the apparatus when said source emits the fan beam.

8. The apparatus of claim 7 wherein said apparatus triggering circuitry includes an external sync circuit for synchronizing said computer means and determining the integration period of said detector means.

9. An apparatus for attaching to a radiation therapy x-ray simulator for computing a CT image, the simulator comprising a radiation source for producing a fan beam, a film holder mounted substantially perpendicularly to the central axis of the fan beam produced by the radiation source, a table for supporting a target object between the radiation source and the film holder, and means for rotating the radiation source and film holder around the target object supported on the table comprising:

a linear detector array adapted for mounting to the film holder of the x-ray simulator with the long axis of said array substantially perpendicular to the central axis of the fan beam produced by the radiation source of the simulator without altering the ability of the simulator to function as a simulator; said detector array comprising a plurality of detector elements, each individual detector element producing an output signal having an amplitude proportional to the energy intensity of the x-ray radiation incident thereon, the intensity of the incident x-ray radiation being proportional to the density of the target object through which the incident x-ray radiation passes before striking the individual detector element; and computer means for scaling the output signal from each detector element to account for the relative distance from the radiation source to the target object and for the distance from the radiation source to said detector array, transforming the output signal from each detector element into the frequency domain for filtering, convolving the filtered signal to produce a signal representing the signal that would have been produced by each detector element had the incident radiation been a parallel beam instead of a fan beam, and converting the transformed signal at each incremental angle into a gray scale value for a picture element having a specific set of coordinates relative to the coordinates of said detector array for output to an appropriate display means.

10. The apparatus of claim 9 additionally comprising circuitry for triggering data collection when radiation is emitted by the radiation source of the x-ray simulator.

11. The apparatus of claim 9 wherein said computer means comprises means for providing a convolved profile for each angular increment by performing a discrete Fourier transform on each scaled signal, multiplying the resulting transforms by increasing values selected from a ramp frequency function to provide scaled transforms for each angular increment, and taking the inverse Fourier transform of each scaled transform to produce the value representing the parallel beam.

12. The apparatus of claim 9 additionally comprising means for correcting the signal at each angular increment for any error caused by a shift in the center of rotation of the radiation source around the target object.

13. The apparatus of claim 12 wherein said shift correcting means comprises an xray opaque rod supported on the table of the x-ray simulator for use as the target object from which any shift in the center of rotation is derived in terms of the number of detector elements.

14. The apparatus of claim 9 wherein said computer means additionally comprises means for correcting the transformed signal for each angular increment for magnification caused by the spread of the fan beam produced by the radiation source of the x-ray simulator.

* * * * *